United States Patent [19]
Katsuno et al.

[11] Patent Number: 4,761,512
[45] Date of Patent: Aug. 2, 1988

[54] CATALYST FOR THE PRODUCTION OF AROMATIC HYDROCARBONS AND PROCESS FOR THE PRODUCTION OF AROMATIC HYDROCARBONS USING SAID CATALYST

[75] Inventors: Hisashi Katsuno, Sodegaura; Takashi Murakawa, Ichihara; Toshikazu Yoneda, Sodegaura, all of Japan

[73] Assignee: Research Association for Utilization of Light Oil, Tokyo, Japan

[21] Appl. No.: 33,077

[22] Filed: Mar. 31, 1987

Related U.S. Application Data

[62] Division of Ser. No. 856,756, Apr. 28, 1986, Pat. No. 4,681,865.

[51] Int. Cl.[4] .................................................. C07C 2/52
[52] U.S. Cl. .................................... 585/417; 708/139; 585/419
[58] Field of Search ................. 585/417, 419; 208/139

[56] References Cited

U.S. PATENT DOCUMENTS

| | | | |
|---|---|---|---|
| 3,691,255 | 9/1972 | Takase et al. | 502/66 |
| 4,324,698 | 4/1982 | Lewis et al. | 502/66 |
| 4,456,527 | 6/1984 | Buss et al. | 208/138 |
| 4,595,669 | 6/1986 | Fung et al. | 502/66 |
| 4,627,912 | 12/1986 | Field | 208/138 |
| 4,648,961 | 3/1987 | Jacobson et al. | 208/138 |

Primary Examiner—Curtis R. Davis
Attorney, Agent, or Firm—Frishauf, Holtz, Goodman & Woodward

[57] ABSTRACT

A process for producing aromatic hydrocarbons which comprises contacting at least one type of hydrocarbon selected from paraffin, olefin, acetylene, cyclic paraffin and cyclic olefin-based hydrocarbons with a catalyst comprising a L-type zeolite treated with a halogen-containing compound and platinum deposited thereon.

16 Claims, 2 Drawing Sheets

CATALYST FOR THE PRODUCTION OF AROMATIC HYDROCARBONS AND PROCESS FOR THE PRODUCTION OF AROMATIC HYDROCARBONS USING SAID CATALYST

This is a division of application Ser. No. 856,756 filed Apr. 28, 1986 now U.S. Pat. No. 4,681,865.

BACKGROUND OF THE INVENTION

The present invention relates to a catalyst for the production of aromatic hydrocarbons and a process for the production of aromatic hydrocarbons using said catalyst. More specifically, it is concerned with a catalyst suitable for use in the production of aromatic hydrocarbons, comprising L-type zeolite treated with a halogen-containing compound and platinum deposited and also with a process for producing aromatic hydrocarbons from various hydrocarbons in high yield and with high efficiency using the above catalyst.

For production of aromatic hydrocarbons from aliphatic hydrocarbons, various methods have been disclosed, including a method using a highly acid zeolite, such as ZSM-5, as a catalyst (see, for example, Japanese Patent Publication Nos. 42639/1981, 23368/1983, Japanese Patent Application Laid-Open Nos. 92717/1978 and 140934/1981), a method using a basic catalyst comprising platinum deposited (see, for example, Japanese Patent Publication No. 57408/1983, Japanese Patent Application Laid-Open Nos. 80333/1984, 133835/1983 and 223614/1983 ), a method using a catalyst which is prepared by oxychlorinating L-type zeolite with a noble metal deposited thereon (Japanese Patent Application Laid-Open No. 168539/1985), a method using crystalline aluminosilicate with platinum and a fluoride deposited thereon (see Japanese Patent Publication No. 16781/1975), and a method in which X, Y or L-type zeolite with a Group VIII metal deposited thereon is used as a catalyst and the reaction is carried out in the presence of halogen (see Japanese Patent Application Laid-Open No. 15489/1985).

These methods, however, have various disadvantages.

For example, the method using a highly acid zeolite catalyst has disadvantages in that large amounts of decomposed gases are formed and the yields of aromatic hydrocarbons are low. The method using a basic catalyst comprising platinum deposited has disadvantages in that the yields of aromatic hydrocarbons are high, but the activity is quickly decreased and thus the catalyst life is undesirably low. In the case of the other methods, the yields of aromatic hydrocarbons are not sufficiently high and the catalyst life is short.

SUMMARY OF THE INVENTION

The present invention is intended to overcome the above problems of the prior art and provides a catalyst which permits production of aromatic hydrocarbons in high yield and has a long service life, and also a process for efficiently producing aromatic hydrocarbons using said catalyst.

It has been found that a catalyst comprising L-type zeolite treated with a halogen-containing compound and platinum deposited thereon is suitable for production of aromatic hydrocarbons and of high practical value. Based on these findings, the present invention has been accomplished.

The present invention relates to a catalyst for the production of aromatic hydrocarbons, comprising L-type zeolite treated with a halogen-containing compound and platinum deposited thereon, and also to a process for the production of aromatic hydrocarbon which comprises contacting at least one type of hydrocarbon selected from paraffin, olefin, acetylene, cyclic paraffin and cyclic olefin hydrocarbons with the above catalyst.

DETAILED DESCRIPTION OF THE INVENTION

Figure 1:
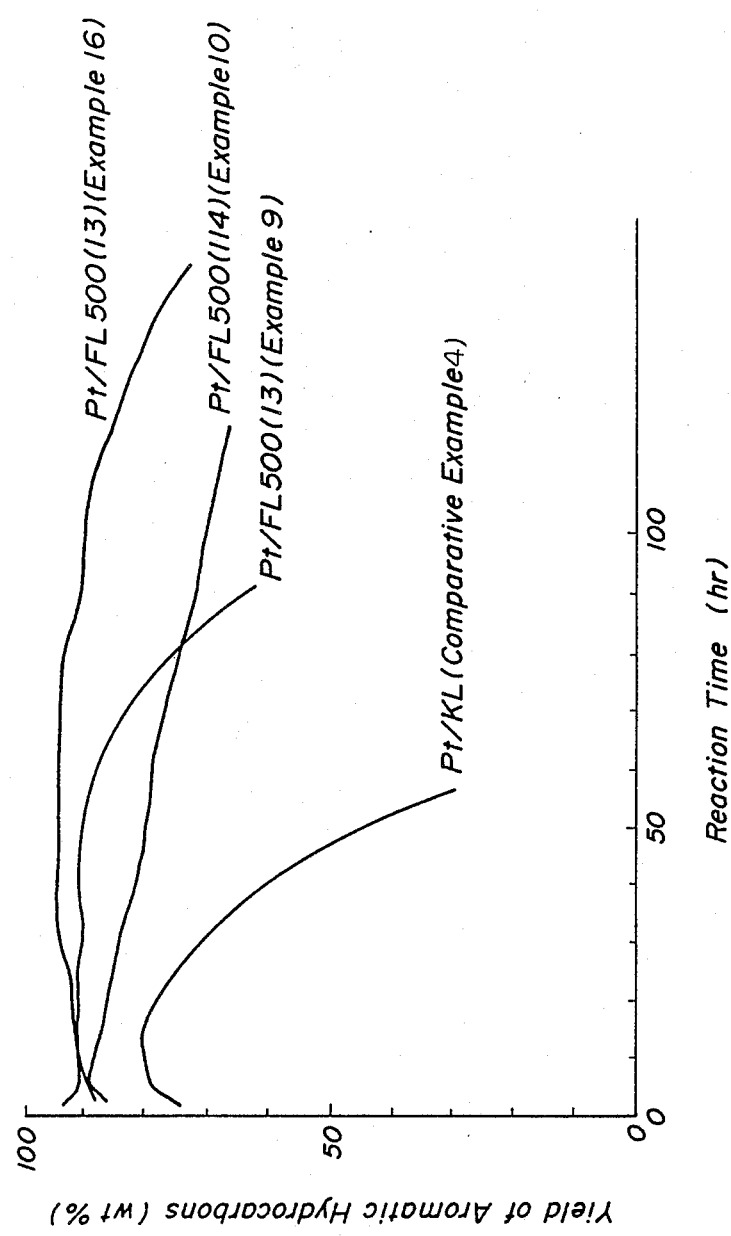
FIG. 1 is a graph showing the relation between the yield of aromatic hydrocarbon and the reaction time for each of Catalyst Pt/FL500(13) prepared in Example 3, Catalyst Pt/FL500(114) prepared in Example 4 and Catalyst Pt/KL prepared in Comparative Example 1 (i.e., Examples 9, 10 and 16, and Comparative Example 4, respectively)
Figure 2:
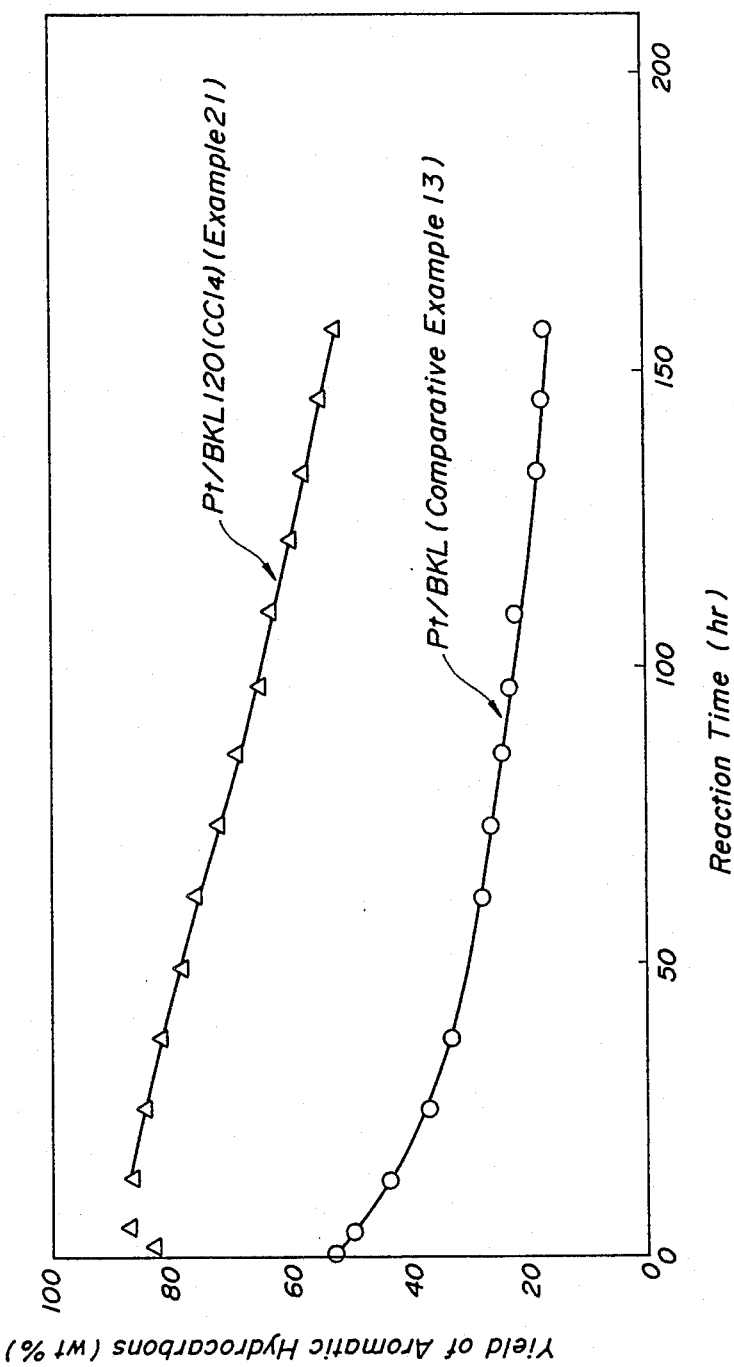
FIG. 2 is a graph showing the relation between the yield of aromatic hydrocarbon and the reaction time for each of Catalyst Pt/BKL120(CCl$_4$) prepared in Example 18 and Catalyst Pt/BKL prepared in Comparative Example 11 (i.e., in Example 21 and Comparative Example 13, respectively).

L-type zeolite which is used in the present invention is represented by the formula:

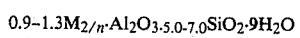

$$0.9\text{--}1.3M_{2/n}\cdot Al_2O_3\cdot 5.0\text{--}7.0SiO_2\cdot 9H_2O$$

(wherein M represents an alkali metal or alkaline earth metal, and n represents the atomic valency of M). This L-type zeolite is described in detail in Japanese Patent Application Laid-Open Nos. 133835/1983 (pp. 9–10) and 80333/1984 (page 5).

In the present invention, the above L-type zeolite is not used as such, but after treating with a halogen-containing compound. Halogen-containing compounds which can be used in the treatment of L-type zeolite include fluorine-containing compounds, chlorine-containing compounds, bromine-containing compounds and iodine-containing compounds. Of these compounds, fluorine-containing compounds and chlorine-containing compounds are preferred. Fluorine-containing compounds are fluorinated hydrocarbons usually called furone gas (fluorene) or fluorinated chlorinated hydrocarbons. Typical examples are trichloromonofluoromethane (CFCl$_3$)(Freon 11), dichlorodifluoromethane (CF$_2$Cl$_2$)(Freon 12), monochlorotrifluoromethane (CF$_3$Cl)(Freon 13), dichloromonofluoromethane (CHFCl$_2$)(Freon 21), monochlorodifluoromethane (CHF$_2$Cl)(Freon 22), trifluoromethane (CHF$_3$)(Freon 23), tetrafluoromethane (CF$_4$)(Freon 14), 1,1,2-trichloro-1,2,2-trifluoroethane (CF$_2$ClCFCl$_2$)(Freon 113) and 1,2-dichloro-1,1,2,2-tetrafluoroethane (CF$_2$ClCF$_2$Cl)(Freon 114).

The chlorine-containing compound includes chlorinated hydrocarbons such as carbon tetrachloride (CCl$_4$), chloroform (CHCl$_3$), dichloromethane (CH$_2$Cl$_2$), hexachloroethane (C$_2$Cl$_6$), tetrachloroethane (C$_2$H$_2$Cl$_4$) and dichloroethane (C$_2$H$_4$Cl$_2$).

Conditions under which L-type zeolite is treated with the aforementioned halogen-containing compound are not critical and can be determined appropriately. It suffices that L-type zeolite is contacted with the halogen-containing compound at a temperature of 80° to 600° C. for a time of 1 minute to 10 hours, preferably 0.5 to 3 hours. When the halogen-containing compound is in a gaseous form, such as furone gas, the L-type zeolite is exposed to an atmosphere of furone gas under the above temperature and time conditions.

The catalyst of the present invention is prepared by depositing platinum on the halogen-containing compound treated L-type zeolite as prepared above. There are no special limitations to the amount of platinum deposited. Usually the amount of platinum deposited is 0.1 to 5.0 wt% (calculated as platinum (Pt)) based on the total weight of the catalyst, with the range of 0.3 to 1.5 wt % being preferred.

Platinum can be deposited on the halogen-containing compound treated L-type zeolite by various methods. In general, the vacuum impregnation method, the ordinary temperature impregnation method, the dipping method, the ion exchange method and so forth can be employed. As a platinum source for the deposition of platinum, various compounds can be used. Typical examples are tetraammineplatinum chloride, chloroplatinic acid, chloroplatinic acid salts, hydroxytetraammine platinum, and dinitroamminoplatinum.

The catalyst of the present invention is used in production of aromatic hydrocarbons from various hydrocarbons in high yield under suitable conditions. In accordance with the process of the present invention, aromatic hydrocarbons can be produced quite efficiently.

As the feedstock for use in the process of the present invention, paraffin hydrocarbons, olefin hydrocarbons, acetylene hydrocarbons, cyclic paraffin hydrocarbons, cyclic olefin hydrocarbons and mixtures thereof can be used. These paraffin hydrocarbons preferably have 6 to 10 carbon atoms. Representative examples of such paraffin hydrocarbons are n-hexane, methylpentane, n-heptane, methylhexane, dimethylpentane, and n-octane.

Typical examples of olefin hydrocarbons are olefins having 6 to 10 carbon atoms, such as hexene, methylpentene, heptene, methylhexene, dimethylpentene and octene.

Typical examples of acetylene hydrocarbons are hydrocarbons having 6 to 10 carbon atoms, such as hexyne, heptyne, and octyne.

Typical examples of cyclic paraffin hydrocarbons are hydrocarbons having 6 to 10 carbon atoms, such as methylcyclopentane, cyclohexane, methylcyclohexane, and dimethylcyclohexane.

Typical examples of cyclic olefin hydrocarbons are hydrocarbons having 6 to 10 carbon atoms, such as methylcyclopentene, cyclohexene, methylcyclohexene, and dimethylcyclohexene.

In accordance with the process of the present invention, the above hydrocarbon feedstock is contacted with the catalyst of the present invention. There are no special limitations to contacting conditions. Good results, however, can be obtained under such conditions that the temperature is 350° to 600° C., preferably 400° to 550° C., the pressure is 0 to 40 kg/cm$^2$G, preferably 0 to 10 kg/cm$^2$G, and LHSV is 0.1 to 20 hr$^{-1}$, preferably 1 to 10 hr$^{-1}$. Much better results can be expected by controlling the hydrogen gas/feed oil ratio (by mole) to 1:1 to 50:1.

As described above, the catalyst of the present invention is of high activity and permits production of aromatic hydrocarbons from various hydrocarbons in high yield, and furthermore has a long service life. Thus the catalyst of the present invention can be effectively used as a catalyst for the production of aromatic hydrocarbons.

In accordance with the process of the present invention, when a saturated hydrocarbon feedstock is used, the desired aromatic hydrocarbon can be almost always produced in a yield as high as not less than 80% and in some cases, in a yield as high as not less than 90%. Furthermore, since the high activity of the catalyst can be maintained for a long time, the yield of the desired aromatic hydrocarbon is very high even if the reaction is continuously carried out for a long time.

Accordingly the present invention is useful in the petrochemical industry in which aromatic hydrocarbons are produced, the petroleum industry in which a high octane value fuel is produced, and so forth.

The present invention is described below in greater detail with reference to the following examples

EXAMPLE 1

Fifteen grams of synthetic L-type zeolite was packed in a quartz reaction tube having a diameter of 20 millimeters. This zeolite was maintained at 500° C. for 1 hour while flowing nitrogen. Then the gas was changed from nitrogen to monochlorotrifluoromethane (CF$^3$Cl) at 300° C., and the zeolite was maintained at 300° C. for 2 hours in a monochlorotrifluoromethane atmosphere to conduct the treatment with a fluorine-containing compound. Then the gas was again changed to nitrogen and the temperature was lowered to room temperature. In this way, a fluorine-containing compound treated L-type zeolite was obtained.

Tetraammineplatinum chloride (Pt(NH$_3$)$_4$Cl$_2$) in the amount of 0.5 wt % (as platinum) based on the weight of the above fluorine-containing compound treated L-type zeolite was dissolved in deionized water of the amount corresponding to the saturated water content of the zeolite to thereby impregnate the zeolite with platinum. After deposition, the zeolite was dried at 80° C. for 3 hours in a hot air drier, pelletized by molding under pressure by the use of a molding machine, pulverized in a mortar, and sieved to 16-32 mesh.

The catalyst thus prepared is called Pt/FL300. The fluorine and chlorine contents of the catalyst are shown in Table 1.

EXAMPLE 2

The procedure of Example 1 was repeated wherein the temperature of the treatment with a fluorine-containing compound was changed to 400° C.

The catalyst thus prepared is called Pt/FL400. The fluorine and chlorine contents of the catalyst are shown in Table 1.

EXAMPLE 3

The procedure of Example 1 was repeated wherein the temperature of the treatment with a fluorine-containing compound was changed to 500° C.

The catalyst thus prepared is called Pt/FL500 (13). The fluorine and chlorine contents of the catalyst are shown in Table 1.

COMPARATIVE EXAMPLE 1

Fifteen grams of synthetic L-type zeolite was packed in a quartz reaction tube having a diameter of 20 millimeters. This zeolite was maintained at 500° C. for 3 hours while flowing nitrogen and then cooled. After cooling, the zeolite was impregnated with a solution of tetraammineplatinum chloride (Pt(NH$_3$)$_4$Cl$_2$) in deionized water of the amount corresponding to the saturated water content of the zeolite. After deposition, the same procedure as in Example 1 was repeated.

The catalyst thus prepared is called Pt/KL.

EXAMPLE 4

The procedure of Example 1 was repeated wherein 1,2-dichloro-1,1,2,2-tetrafluoroethane ($CF_2ClCF_2Cl$) was used in place of monochlorotrifluoromethane ($CF_3Cl$) and the temperature of the treatment with a fluorine-containing compound was changed to 500° C.

The catalyst thus prepared is called Pt/FL500 (114). The fluorine and chlorine contents of the catalyst are shown in Table 1.

TABLE 1

| Example No. | Name of Catalyst | Each Component Content of Catalyst (wt %) | |
|---|---|---|---|
| | | F | Cl |
| 1 | Pt/FL300 | 0.07 | 0.05 |
| 2 | Pt/FL400 | 0.14 | 0.12 |
| 3 | Pt/FL500(13) | 0.5 | 0.5 |
| 4 | Pt/FL500(114) | 0.3 | 0.4 |

EXAMPLE 5

Thirty grams of synthetic L-type zeolite and 300 milliliters of a 1N rubidium chloride solution as an ion exchange solution were contacted for 3 hours by stirring while heating at 80° C. The solid product thus obtained was filtered off, washed with deionized water until no chlorine ion could be detected, and then dried at 120° C. for 3 hours to prepare a rubidium-L-type zeolite catalyst.

Thereafter the procedure of Example 1 was repeated wherein the above rubidium-L-type zeolite catalyst was used in place of the synthetic L-type zeolite and the temperature of the treatment with a fluorine-containing compound was changed to 500° C.

The catalyst thus prepared is called Pt/FRbL500.

EXAMPLE 6

The procedure of Example 5 was repeated wherein a solution of cesium chloride was used in place of the rubidium chloride solution.

The catalyst thus prepared is called Pt/FCsL500.

COMPARATIVE EXAMPLE 2

The procedure of Example 5 was repeated wherein the treatment with a fluorine-containing compound was not applied.

The catalyst thus prepared is called Pt/RbL.

COMPARATIVE EXAMPLE 3

The procedure of Example 6 was repeated wherein the treatment with a fluorine-containing compound was not applied.

The catalyst thus prepared is called Pt/CsL.

EXAMPLES 7 TO 12

The reaction of conversion of hydrocarbon was performed using the catalysts prepared in Examples 1 to 6.

That is, 0.5 gram of each catalyst (16–32 mesh) was packed in a quartz reaction tube, and then heated to 300° C. and calcined for 1 hour while flowing air. Then the air was replaced with nitrogen, and the catalyst was heated to 500° C. and reduced with hydrogen for 1 hour.

A hydrogen/n-hexane (5/1 by mole) feedstock was passed through the above reaction tube and reacted under the conditions of weight hourly space velocity (WHSV), 2.0 per hour ($hr^{-1}$), pressure, 5 kilograms per square centimeter by gauge ($kg/cm^2G$), and temperature, 500° C. The results are shown in Table 2.

The relation between the reaction time and the yield of aromatic hydrocarbon for each of Catalysts Pt/FL500 (13) and Pt/FL500 (114) prepared in Examples 3 and 4, respectively, is shown in FIG. 1.

COMPARATIVE EXAMPLES 4 TO 6

The procedure of Example 7 was repeated wherein the catalysts prepared in Comparative Examples 1 to 3 were each used in place of the catalyst of Example 7. The results are shown in Table 2.

The relation between the reaction time and the yield of aromatic hydrocarbon for Catalyst Pt/KL prepared in Comparative Example 1 is shown in FIG. 1.

EXAMPLE 13

The procedure of Example 7 was repeated wherein Catalyst Pt/FL500 (13) prepared in Example 3 was used as a catalyst and as the feedstock, n-heptane or n-octane was used. The results are shown in Table 3.

EXAMPLE 14

The procedure of Example 7 was repeated wherein Catalyst Pt/FL500 (13) prepared in Example 3 was used as a catalyst and as the feedstock, heavy naphtha having properties as shown below was used. The results are shown in Table 4.

| Properties of Heavy Naphtha | | |
|---|---|---|
| Distillation | Initial Boiling Temperature (IBP) | 89° C. |
| | 10% Boiling Temperature | 102° C. |
| | 30% Boiling Temperature | 110° C. |
| | 50% Boiling Temperature | 119° C. |
| | 70% Boiling Temperature | 131° C. |
| | 90% Boiling Temperature | 146° C. |
| | 95% Boiling Temperature | 152° C. |
| | End Temperature (EP) | 161° C. |
| Specific Gravity | (15/4° C.) | 0.7429 |
| Composition (%) | Paraffins | 65.7 |
| | Naphthenes | 20.8 |
| | Olefins | 0 |
| | Aromatics | 13.5 |

COMPARATIVE EXAMPLES 7 AND 8

The procedure of Example 14 was repeated wherein Catalyst Pt/KL in Comparative Example 1 and a commercially available catalyst, Pt·Re/$Al_2O_3$ (naphth reforming catalyst), were each used as a catalyst. The results are shown in Table 4.

EXAMPLE 15

The procedure of Example 7 was repeated wherein Catalyst Pt/FL500 prepared in Example 3 was used as a catalyst and as the feedstock, a mixture of hydrocarbons having 6 carbon atoms as shown below was used. The results are shown in Table 5.

| | |
|---|---|
| 2-Methylpentane | 23.9 wt % |
| 3-Methylpentane | 17.1 wt % |
| n-Hexane | 50.7 wt % |

| | |
|---|---|
| -continued | |
| Methylcyclopentane | 8.3 wt % |

COMPARATIVE EXAMPLE 9

The procedure of Example 15 was repeated wherein Catalyst Pt/KL prepared in Comparative Example 1 was used as a catalyst. The results are shown in Table 5.

EXAMPLE 16

The procedure of Example 7 was repeated wherein Catalyst Pt/FL500 (13) prepared in Example 3 was used as a catalyst and the pressure was changed to 2 kg/cm$^2$G. The relation between the reaction time and the yield of aromatic hydrocarbon is shown in FIG. 1.

EXAMPLE 17

Fifteen grams of synthetic L-type zeolite was packed in a quartz reaction tube having a diameter of 20 millimeters. The zeolite was maintained at 500° C. for 1 hour while flowing nitrogen and then cooled to 150° C. Then nitrogen was bubbled through carbon tetrachloride, and this carbon tetrachloride was introduced in the reaction tube to carry out the treatment with a chlorine-containing compound. Thereafter the gas was changed to nitrogen and then the temperature was lowered to room temperature to prepare a chlorine-containing compound treated L-type zeolite. Tetraammineplatinum chloride (Pt(NH$_3$)$_4$Cl2) in the amount of 0.5 wt % (as platinum) based on the weight of the above chlorine-containing compound treated L-type zeolite was dissolved in deionized water of the amount corresponding to the saturated water content of the zeolite, and the zeolite was impregnated with platinum. After deposition, the zeolite was dried at 80° C. for 3 hours in a hot air drier, pelletized by molding under pressure by the use of a molding machine, pulverized in a mortar and then sieved to 16–32 mesh.

The catalyst thus prepared is called Pt/KL150 (CCl$_4$).

TABLE 2

| | | EXAMPLE 7 | EXAMPLE 8 | EXAMPLE 9 | COMPARATIVE EXAMPLE 4 | EXAMPLE 10 | EXAMPLE 11 | COMPARATIVE EXAMPLE 5 | EXAMPLE 12 | COMPARATIVE EXAMPLE 6 |
|---|---|---|---|---|---|---|---|---|---|---|
| Catalyst | | Pt/FL300 | Pt/FL400 | Pt/FL500 (13) | Pt/KL | Pt/FL500 (114) | Pt/FRbL500 | Pt/RbL | Pt/FCsL500 | Pt/FCsL500 |
| Reaction Time (hr) | | 4 | 4 | 4 | 4 | 4 | 4 | 4 | 4 | 4 |
| Conversion of n-hexane (wt %) | | 99.7 | 99.4 | 99.8 | 99.3 | 99.7 | 99.8 | 99.9 | 99.8 | 99.7 |
| Selectivity (wt %) | C$_1$-C$_4$ Hydrocarbons | 13.2 | 5.6 | 6.8 | 15.6 | 6.6 | 9.9 | 18.1 | 18.2 | 21.4 |
| | C$_5$+ Hydrocarbons | 86.8 | 94.4 | 93.2 | 84.4 | 93.4 | 90.1 | 81.9 | 81.8 | 78.6 |
| | Aromatic Hydrocarbons | 81.1 | 86.6 | 89.6 | 79.3 | 89.3 | 85.6 | 75.9 | 76.4 | 72.1 |
| Yield of Aromatic Hydrocarbons (wt %) | | 81.8 | 86.1 | 89.5 | 78.7 | 89.0 | 85.5 | 75.8 | 76.2 | 71.9 |

TABLE 3

| | | EXAMPLE 13 | |
|---|---|---|---|
| Catalyst | | Pt/FL500 (13) | |
| Starting Material | | n-heptane | n-octane |
| Reaction Time (hr) | | 11 | 11 |
| Conversion of Starting Material (wt %) | | 100.0 | 99.8 |
| Selectivity (wt %) | C$_1$-C$_4$ Hydrocarbon | 7.9 | 12.8 |
| | C$_5$+ Hydrocarbon | 92.1 | 87.2 |
| | Aromatic Hydrocarbon | 90.9 | 84.9 |
| Composition of Aromatic Hydrocarbon (wt %) | C$_6$ Aromatic Hydrocarbon | 25.4 | 20.0 |
| | C$_7$ Aromatic Hydrocarbon | 74.2 | 32.5 |
| | C$_8$ Aromatic Hydrocarbon | 0.0 | 47.5 |
| | C$_9$+ Aromatic Hydrocarbon | 0.4 | 0.0 |

TABLE 4

| | | EXAMPLE 14 | COMPARATIVE EXAMPLE 7 | COMPARATIVE EXAMPLE 8 |
|---|---|---|---|---|
| Catalyst | | Pt/FL500 (13) | Pt/KL | Pt.Re/Al$_2$O$_3$ |
| Reaction Time (hr) | | 4 | 4 | 4 |
| Selectivity (wt %) | C$_1$-C$_4$ Hydrocarbon | 8.8 | 12.3 | 13.4 |
| | C$_5$+ Hydrocarbon | 91.2 | 87.7 | 86.6 |
| | Aromatic Hydrocarbon | 89.0 | 81.4 | 65.1 |
| Composition of Aromatic Hydrocarbon (wt %) | C$_6$ Aromatic Hydrocarbon | 19.8 | 26.0 | 8.9 |
| | C$_7$ Aromatic Hydrocarbon | 44.2 | 43.0 | 36.1 |
| | C$_8$ Aromatic Hydrocarbon | 27.5 | 22.5 | 38.7 |
| | C$_9$+ Aromatic Hydrocarbon | 8.5 | 8.5 | 16.3 |

TABLE 5

| | | EXAMPLE 15 | COMPARATIVE EXAMPLE 9 |
|---|---|---|---|
| Catalyst | | Pt/FL500(13) | Pt/KL |
| Reaction Time (hr) | | 4 | 4 |
| Selectivity (wt %) | C$_1$-C$_4$ Hydrocarbon | 13.4 | 21.1 |
| | C$_5$+ Hydrocarbon | 86.6 | 78.9 |
| | Aromatic Hydrocarbon | 84.0 | 69.8 |

EXAMPLE 18

Five grams of silica binder molded L-type zeolite (spherical; average diameter: 0.5 millimeter) was dipped in 12 grams of carbon tetrachloride, and the treatment with a chlorine-containing compound is carried out in a hot air drier which had been preheated to 120° C. to prepare a chlorine-containing compound treated L-type zeolite. Thereafter the same procedure as in Example 1 was repeated to prepare a catalyst comprising the above L-type zeolite with platinum deposited thereon.

This catalyst is called Pt/BKL120(CCl$_4$).

EXAMPLE 19

The procedure of Example 18 was repeated wherein the treatment with a chlorine-containing compound was performed at 150° C.

The catalyst thus prepared is called Pt/BKL150(CCl$_4$). The chlorine content of the catalyst was 0.4 wt %.

COMPARATIVE EXAMPLE 10

The procedure of Example 17 was repeated wherein the treatment with a chlorine-containing compound was not applied.

The catalyst thus prepared is called Pt/KL.

COMPARATIVE EXAMPLE 11

The procedure of Example 18 was repeated wherein the treatment with a chlorine-containing compound was not applied.

The catalyst thus prepared is called Pt/BKL.

EXAMPLE 20, AND COMPARATIVE EXAMPLE 12

The reaction of conversion of n-hexane was performed in the same manner as in Example 7 except that the catalysts prepared in Example 17 and Comparative Example 10 were each used as a catalyst. The results are shown in Table 6.

TABLE 6

|  |  | EXAMPLE 20 |  | COMPARATIVE EXAMPLE 12 |  |
|---|---|---|---|---|---|
| Catalyst |  | Pt/KL150(CCl$_4$) |  | Pt/KL |  |
| Reaction Time (hr) |  | 4 | 4 | 4 | 4 |
| Reaction Temperature (°C.) |  | 475 | 500 | 475 | 500 |
| Conversion of n-hexane (wt %) |  | 99.1 | 99.6 | 98.6 | 99.7 |
| Selectivity (wt %) | C$_1$–C$_4$ Hydrocarbon | 16.3 | 12.0 | 14.2 | 13.9 |
|  | C$_5$ Hydrocarbon | 7.7 | 3.4 | 7.9 | 4.9 |
|  | C$_6^+$ Hydrocarbon | 0.8 | 1.7 | 4.4 | 1.5 |
|  | Aromatic Hydrocarbon | 75.2 | 82.8 | 73.5 | 79.8 |
| Yield of Aromatic Hydrocarbon (wt %) |  | 74.6 | 82.5 | 72.5 | 79.5 |

EXAMPLES 21 AND 22, AND COMPARATIVE EXAMPLE 13

The reaction of conversion of n-hexane was performed in the same manner as in Example 7 except that the catalysts prepared in Examples 18 and 19, and Comparative Example 11 were each used as a catalyst. The results are shown in Table 7. The relation between the reaction time and the yield of aromatic hydrocarbon for each of Catalyst Pt/BKL120 (CCl$_4$) prepared in Example 18 and Catalyst Pt/BKL prepared in Comparative Example 11 is shown in Table 2.

TABLE 7

|  | EXAMPLE 21 | EXAMPLE 22 |  | COMPARATIVE EXAMPLE 13 |  |
|---|---|---|---|---|---|
| Catalyst | Pt/BKL120(CCl$_4$) | Pt/BKL150(CCl$_4$) |  | Pt/BKL |  |
| Reaction Time (hr) | 4 | 4 | 4 | 4 | 4 |
| Reaction Temperature (°C.) | 500 | 475 | 500 | 475 | 500 |
| Conversion of n-hexane (wt %) | 99.7 | 97.8 | 99.6 | 68.2 | 87.2 |
| Selectivity (wt %) |  |  |  |  |  |
| C$_1$–C$_4$ Hydrocarbon | 7.3 | 8.8 | 10.2 | 6.5 | 7.3 |
| C$_5$ Hydrocarbon | 3.9 | 5.5 | 4.1 | 4.7 | 5.9 |
| C$_6^+$ Hydrocarbon | 1.5 | 7.8 | 1.5 | 38.3 | 29.8 |
| Aromatic Hydrocarbon | 87.3 | 77.8 | 84.2 | 50.5 | 56.9 |
| Yield of Aromatic Hydrocarbon (wt %) | 87.1 | 76.1 | 83.8 | 34.4 | 49.6 |

EXAMPLE 23

The procedure of Example 18 was repeated wherein the treatment with a chlorine-containing compound was performed with chloroform (CHCl$_3$).

The catalyst thus prepared is called Pt/BKL120(CHCl$_3$).

EXAMPLE 24

The procedure of Example 18 was repeated wherein the treatment with a chlorine-containing compound was performed with 2-dichloroethane (CH$_2$ClCH$_2$Cl).

The catalyst thus prepared is called Pt/BKL120(CH$_2$ClCH$_2$Cl).

EXAMPLE 25

The procedure of Example 18 was repeated wherein the treatment with a chlorine-containing compound was performed at 300° C.

The catalyst thus prepared is called Pt/BKL300(CCl$_4$).

EXAMPLES 26 TO 28

The reaction of conversion of n-hexane was performed in the same manner as in Example 7 except that the catalysts prepared in Examples 23 to 25 were each used as a catalyst. The results are shown in Table 8.

TABLE 8

|  | EXAMPLE 26 | EXAMPLE 27 | EXAMPLE 28 |
|---|---|---|---|
| Catalyst | Pt/BKL120(CHCl$_3$) | Pt/BKL120(CH$_2$ClCH$_2$Cl) | Pt/BKL300(CCl$_4$) |
| Reaction Time (hr) | 4 | 4 | 4 |

TABLE 8-continued

|  | EXAMPLE 26 | EXAMPLE 27 | EXAMPLE 28 |
|---|---|---|---|
| Reaction Temperature (°C.) | 500 | 500 | 500 |
| Conversion of n-hexane (wt %) | 99.7 | 99.7 | 99.3 |
| Selectivity $C_1$–$C_4$ Hydrocarbon | 7.7 | 8.9 | 6.8 |
| (wt %) $C_5$ Hydrocarbon | 3.7 | 3.9 | 4.0 |
| $C_6{}^+$ Hydrocarbon | 3.5 | 3.5 | 3.0 |
| Aromatic Hydrocarbon | 85.1 | 83.7 | 86.2 |
| Yield of Aromatic Hydrocarbon (wt %) | 84.9 | 83.4 | 85.6 |

We claim:

1. A process for producing aromatic hydrocarbons which comprises contacting at least one type of hydrocarbon selected from paraffin, olefin, acetylene, cyclic paraffin and cyclic olefin-based hydrocarbons with a cataylyst comprising zeolite L treated with a halogen-containing compound and platinum, said catalyst having been formed by treating zeolite L with said halogen-containing compound to form a halogen-treated zeolite L and then depositing platinum thereon.

2. The process as claimed in claim 1, wherein the halogen-containing compound is a fluorine-containing compound.

3. The process as claimed in claim 1, wherein the halogen-containing compound is a chlorine-containing compound.

4. The process as claimed in claim 1, wherein the amount of platinum deposited is 0.1 to 5.0 wt % based on the total weight of the catalyst.

5. The process as claimed in claim 1, wherein contacting the hydrocarbon with the catalyst is carried out under the conditions of temperature 350°–600° C., pressure 0–40 kg/cm$^2$G and liquid hourly space velocity 0.1–20 hr$^{-1}$.

6. The process as claimed in claim 1, wherein said halogen-containing compound is a fluorinated hydrocarbon.

7. The process as claimed in claim 1, wherein said halogen-containing compound is a chlorinated hydrocarbon.

8. The process as claimed in claim 1, wherein said halogen-containing compound is a fluorinated chlorinated hydrocarbon.

9. The process as claimed in claim 1, wherein said halogen-containing compound is fluorene.

10. The process as claimed in claim 1, wherein said halogen-containing compound is $CFCl_3$, $CF_2Cl_2$, $CF_3Cl$, $CHFCl_2$, $CHF_2Cl$, $CHF_3$, $CF_4$, $CF_2ClCFCl_2$ and $CF_2ClCF_2Cl$.

11. The process as claimed in claim 1, wherein said halogen-containing compound is $CCl_4$, $CHCl_3$, $CH_2Cl_2$, $C_2Cl_6$, $C_2H_2Cl_4$ amd $C_2H_4Cl_2$.

12. The process as claimed in claim 1, wherein the amount platinum deposited is 0.3 to 1.5 wt % based on the total weight of the catalyst.

13. The process as claimed in claim 9, wherein said zeolite L which has been treated with said halogen-containing compound is then immersed in a solution of tetraamineplatinum chloride and from 0.3 to 1.5 wt % of platinum based on the total weight of the catalyst is deposited thereon.

14. The process as claimed in claim 10, wherein said zeolite L which has been treated with said halogen-containing compound is then immersed in a solution of tetraamineplatinum chloride and from 0.3 to 1.5 wt % of platinum based on the total weight of the catalyst is deposited thereon.

15. The process as claimed in claim 11, wherein said zeolite L which has been treated with said halogen-containing compound is then immersed in a solution of tetraammineplatinum chloride and from 0.3 to 1.5 wt % of platinum based on the total weight of the catalyst is deposited thereon.

16. The process as claimed in claim 1, wherein said platinum is deposited thereon by immersing said halogen-compound treated catalyst L in a solution having a platinum compound dissolved therein.

* * * * *